United States Patent
Inoue et al.

(10) Patent No.: US 12,408,901 B2
(45) Date of Patent: Sep. 9, 2025

(54) INTRAUTERINE TISSUE COLLECTION INSTRUMENT

(71) Applicant: Kitazato Corporation, Fuji (JP)

(72) Inventors: Futoshi Inoue, Fujinomiya (JP); Chie Inaba, Fujinomiya (JP)

(73) Assignee: KITAZATO CORPORATION, Fuji (JP)

( * ) Notice: Subject to any disclaimer, the term of this patent is extended or adjusted under 35 U.S.C. 154(b) by 785 days.

(21) Appl. No.: 17/665,124

(22) Filed: Feb. 4, 2022

(65) Prior Publication Data

US 2022/0151594 A1 May 19, 2022

Related U.S. Application Data

(63) Continuation of application No. PCT/JP2020/030075, filed on Aug. 5, 2020.

(30) Foreign Application Priority Data

Aug. 6, 2019 (JP) .................................. 2019-144462

(51) Int. Cl.
*A61B 10/02* (2006.01)

(52) U.S. Cl.
CPC ...... *A61B 10/0291* (2013.01); *A61B 10/0283* (2013.01)

(58) Field of Classification Search
CPC .................. A61B 10/0291; A61B 10/0283
See application file for complete search history.

(56) References Cited

U.S. PATENT DOCUMENTS 4,877,037 A    10/1989    Ko et al.
5,069,224 A  * 12/1991    Zinnanti, Jr. ...... A61B 10/0291
                                                               604/38

(Continued)

FOREIGN PATENT DOCUMENTS

CN        202060807 U    12/2011
CN        207024353 U     2/2018

(Continued)

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA/237) issued Feb. 17, 2022, by the International Bureau of WIPO in corresponding International Application No. PCT/JP2020/030075. (7 pages).

(Continued)

*Primary Examiner* — Charles A Marmor, II
*Assistant Examiner* — Severo Antonio P. Lopez
(74) *Attorney, Agent, or Firm* — BUCHANAN INGERSOLL & ROONEY PC (57) ABSTRACT

An intrauterine tissue collecting instrument includes a flexible outer tube, a flexible inner tube within the outer tube, and a shaft member within the inner tube. The flexible outer tube includes an outer tube distal end portion that can be open at at least three slits 4. The flexible inner tube includes an inner tube distal end portion including a plurality of side openings. The shaft member includes a diameter-expanded distal end portion. The intrauterine tissue collecting instrument can collect intrauterine tissue through suction in a state where the inner tube protrudes from the outer tube within the uterus. The inner tube distal end portion can be housed again in the flexible outer tube within the uterus.

12 Claims, 11 Drawing Sheets

(56) References Cited

U.S. PATENT DOCUMENTS

| | | | | |
|---|---|---|---|---|
| 5,464,022 A | * | 11/1995 | Mohajer | A61B 10/0291 |
| | | | | 604/38 |
| 6,042,552 A | | 3/2000 | Cornier | |
| 2003/0055373 A1 | * | 3/2003 | Sramek | A61B 10/0275 |
| | | | | 604/19 |
| 2005/0137448 A1 | * | 6/2005 | Wingler | A61B 10/0291 |
| | | | | 600/34 |
| 2007/0106174 A1 | * | 5/2007 | Sanders | A61B 17/42 |
| | | | | 604/38 |
| 2007/0173736 A1 | | 7/2007 | Feuer et al. | |
| 2008/0045924 A1 | | 2/2008 | Cox et al. | |

FOREIGN PATENT DOCUMENTS

| | | |
|---|---|---|
| JP | S63127745 A | 5/1988 |
| JP | S63501273 A | 5/1988 |
| JP | H10508240 A | 8/1998 |
| WO | 2007/044833 A2 | 4/2007 |
| WO | 2007/044833 A3 | 4/2007 |

OTHER PUBLICATIONS

The extended European Search Report issued Aug. 3, 2022, by the European Patent Office in corresponding European Patent Application No. 20850577.6-1122. (9 pages).

International Search Report (PCT/ISA/210) with translation and Written Opinion (PCT/ISA/237) mailed on Sep. 15, 2020, by the Japan Patent Office as the International Searching Authority for International Application No. PCT/JP2020/030075. (12 pages).

* cited by examiner

INTRAUTERINE TISSUE COLLECTION INSTRUMENT

TECHNICAL FIELD

The present invention relates to an intrauterine tissue collecting instrument for collecting intrauterine tissue such as fragments of endometrium, uterine mucosa, or uterine mucus through suction.

BACKGROUND ART

In tests for corpus uteri cancer, histological diagnosis is carried out by collecting intrauterine tissue and using the collected tissue as a specimen. When collecting endometrial tissue for histological diagnosis, a metal rod-shaped instrument that is called a sonde curette is inserted into the uterus, and tissue within the uterus is scraped (curetted) using a blade that is provided at a distal end of the instrument. However, the uterus is inclined toward the urinary bladder, and the opening of the uterus (specifically, a portion from the vagina to the internal os of uterus) is bent. Therefore, it is often difficult to insert the sonde curette linearly into the opening of the uterus. Accordingly, there are not a few cases where a sufficient amount of tissue cannot be collected at once when collecting endometrial tissue and collection of the tissue needs to be performed a plurality of times.

Intrauterine tissue collecting instruments for collecting tissue through suction, unlike the above-described sonde curette, have been proposed. JP H10-508240A (Patent Document 1) describes an example of intrauterine tissue collecting instruments for collecting tissue through suction.

An intrauterine tissue collecting instrument described in Patent Document 1 includes: a tube (2) having an open proximal end (a portion that is furthest from the patient) and an opposite (distal) end (4) that is sealed except for a suction aperture (5); and a sealed plunger adapted to move in the tube (2) and connected to a distal end of a rod (8) whose proximal end (on the side opposite to the patient) is provided with a gripping member (9). Means (10) for enhancing and increasing the mechanical action of collection of the tube from the wall is provided at the distal end (4) of the tube (2) adjacent to the suction aperture (5).

Generally single use of this known device is as follows. That is, the device is introduced through the patient's cervix up to the fundus uteri. Graduations provided on the tube make it possible to localize the arrival of the distal end of the tube (provided with the aperture) at the beginning of the uterine cavity. The operator, while holding the tube and pulling on the rod, by the gripping member, in the direction of removal with respect to the patient, produces negative pressure inside the tube and therefore a phenomenon of suction at the level of the aperture disposed at the distal end of the tube. Fragments of the uterine wall and fragments of uterine mucous membrane are collected by displacing the tube, preferably by longitudinal reciprocating movement and rotation about the longitudinal axis, while maintaining the distal end of the tube against the wall. Fragments of the mucous membrane are therefore torn from the wall and are sucked into the tube through the suction aperture.

CITATION LIST

Patent Documents

Patent Document 1: JP H10-508240A (WO97-19642, USP6042552)

SUMMARY OF INVENTION

Technical Problem

Intrauterine tissue can be collected relatively easily using the intrauterine tissue collecting instrument described in Patent Document 1. However, the intrauterine tissue collecting instrument that has collected intrauterine tissue passes through the vagina and the like after collecting the tissue, and accordingly, matter other than the intrauterine tissue may be attached to an external surface of the instrument or may enter the inside of the instrument from an opening, and a good test specimen cannot always be collected.

The present invention has an object of providing an intrauterine tissue collecting instrument that can prevent collected intrauterine tissue and an external surface of the instrument from being contaminated by matter other than the intrauterine tissue and that makes it possible to easily collect intrauterine tissue that serves as a good test specimen.

Solution to Problem

The above-described object can be achieved by the following.

An intrauterine tissue collecting instrument comprising:
a flexible outer tube of which a distal end portion can be inserted into the uterus;
a flexible inner tube that is inserted into the flexible outer tube and is movable within the flexible outer tube in an axial direction; and
a shaft member that is inserted into the flexible inner tube and is movable within the flexible inner tube in an axial direction,
wherein the flexible outer tube includes an outer tube distal end portion that can be open and includes a substantially semispherical distal end and at least three slits that extend from substantially the center of the distal end toward a proximal end and in the direction of a side surface and are arranged at substantially equal angles with respect to a center axis of the flexible outer tube,
the flexible inner tube includes an inner tube distal end portion that includes a closed distal end and a plurality of side openings that are provided on a proximal end side with respect to the closed distal end,
the shaft member includes a diameter-expanded distal end portion that slides within the flexible inner tube in a liquid-tight manner and a core, the diameter-expanded distal end portion being a flare-shaped diameter-expanded portion of which the diameter increases toward a distal end, the shaft member has a higher resistance to movement toward the distal end side in the flexible inner tube than toward the proximal end side in the flexible inner tube,
the flexible outer tube allows the inner tube distal end portion to protrude from the outer tube distal end portion by spreading slits formed portion when the flexible inner tube is pushed, and
the intrauterine tissue collecting instrument can collect intrauterine tissue through suction via the side openings of the flexible inner tube when the shaft member is moved toward the proximal end in a state where the inner tube distal end portion protrudes from the outer tube distal end portion within the uterus, and the inner tube distal end portion protruding from the outer tube distal end portion can be housed again in the flexible outer tube within the uterus by moving the flexible inner tube toward the proximal end.

DESCRIPTION OF EMBODIMENTS

An intrauterine tissue collecting instrument according to the present invention will be described using an embodiment shown in the drawings.

An intrauterine tissue collecting instrument 1 according to the present invention is an intrauterine tissue collecting instrument of which a distal end portion can be inserted into the uterus. The intrauterine tissue collecting instrument 1 includes a flexible outer tube 2 of which a distal end portion can be inserted into the uterus, a flexible inner tube 3 that is inserted into the flexible outer tube 2 and is movable within the flexible outer tube 2 in an axial direction, and a shaft member 4 that is inserted into the flexible inner tube 3 and is movable within the flexible inner tube 3 in an axial direction. The flexible outer tube 2 includes an outer tube distal end portion 23 that can be open and includes a substantially semispherical distal end 23*a* and at least three slits 24 that extend from substantially the center of the distal end 23*a* toward a proximal end and in the direction of a side surface and are arranged at substantially equal angles with respect to the center axis of the flexible outer tube 2. The flexible inner tube 3 includes an inner tube distal end portion 33 that includes a closed distal end and a plurality of side openings 34*a*, 34*b*, 35*a*, and 35*b* provided on the proximal end side with respect to the closed distal end. The shaft member 4 includes a diameter-expanded distal end portion 45 that slides within the flexible inner tube 3 in a liquid-tight manner and a core (inner core) 43. The diameter-expanded distal end portion 45 is a flare-shaped diameter-expanded portion of which the diameter increases toward the distal end. The shaft member 4 has a higher resistance to movement toward the distal end side in the flexible inner tube 3 than toward the proximal end side in the flexible inner tube 3. The flexible outer tube 2 allows the inner tube distal end portion 33 to protrude from the outer tube distal end portion 23 by spreading slits 24 formed portion when the flexible inner tube 3 is pushed. The intrauterine tissue collecting instrument 1 can collect intrauterine tissue 5 through suction via the side openings 34*a*, 34*b*, 35*a*, and 35*b* of the flexible inner tube 3 when the shaft member 4 is moved toward the proximal end in the state where the inner tube distal end portion 33 protrudes from the outer tube distal end portion 23 within the uterus, and the inner tube distal end portion 33 protruding from the outer tube distal end portion 23 can be housed again in the flexible outer tube 2 within the uterus by moving the flexible inner tube 3 toward the proximal end.

Also, In the intrauterine tissue collecting instrument 1, a resistance to movement of the shaft member 4 within the flexible inner tube 3 toward the distal end is higher than a resistance to movement of the shaft member 4 within the flexible inner tube 3 toward the proximal end. When the flexible inner tube 3 is pushed into the flexible outer tube 2, a portion of the flexible outer tube 2 provided with the slits 24 spreads and allows the inner tube distal end portion 33 to protrude from the outer tube distal end portion 23. When the shaft member 4 is moved toward the proximal end in the state where the inner tube distal end portion 33 protrudes from the outer tube distal end portion 23 within the uterus, the intrauterine tissue collecting instrument 1 can collect intrauterine tissue 5 through suction via the side openings 34*a*, 34*b*, 35*a*, and 35*b* of the flexible inner tube 3, and the inner tube distal end portion 33 protruding from the outer tube distal end portion 23 can be housed again in the flexible outer tube 2 within the uterus by moving the flexible inner tube 3 toward the proximal end.

The intrauterine tissue collecting instrument 1 according to the present invention includes the flexible outer tube 2 of which the distal end portion can be inserted into the uterus, the flexible inner tube 3 that is inserted into the flexible outer tube 2 and is movable within the flexible outer tube 2 in the axial direction, and the shaft member 4 that is inserted into the flexible outer tube 3 and is movable within the flexible inner tube 3 in the axial direction.

As shown in FIGS. 1 to 5, the flexible outer tube 2 includes an outer tube main body 21, the outer tube distal end portion 23 that is formed at the distal end of the outer tube main body 21, an outer tube hub 22 that is provided in a rear end portion of the outer tube main body 21, and a lumen 25.

Figure 4:
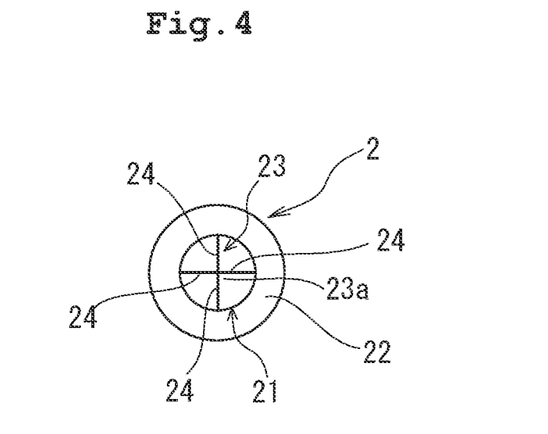
FIG. 4 is a plan view of the flexible outer tube shown in FIG. 3.
Figure 5:
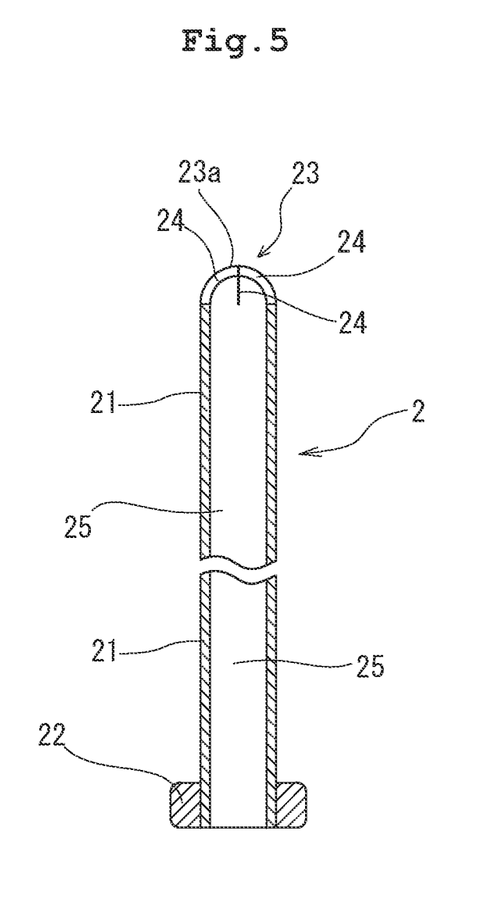
FIG. 5 is a longitudinal cross-sectional view of the flexible outer tube shown in FIG. 3.
Figure 6:
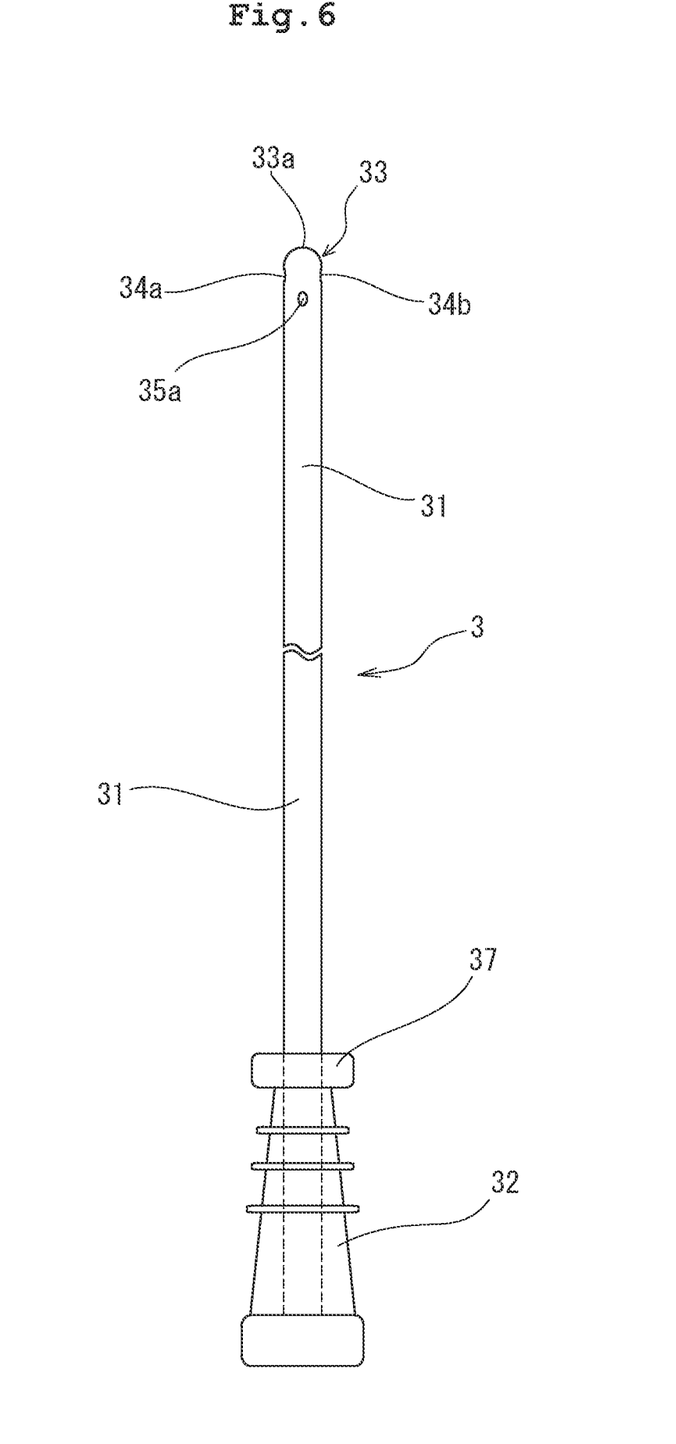
FIG. 6 is a partially omitted enlarged front view of a flexible inner tube that is used in the intrauterine tissue collecting instrument shown in FIG. 1.
Figure 7:
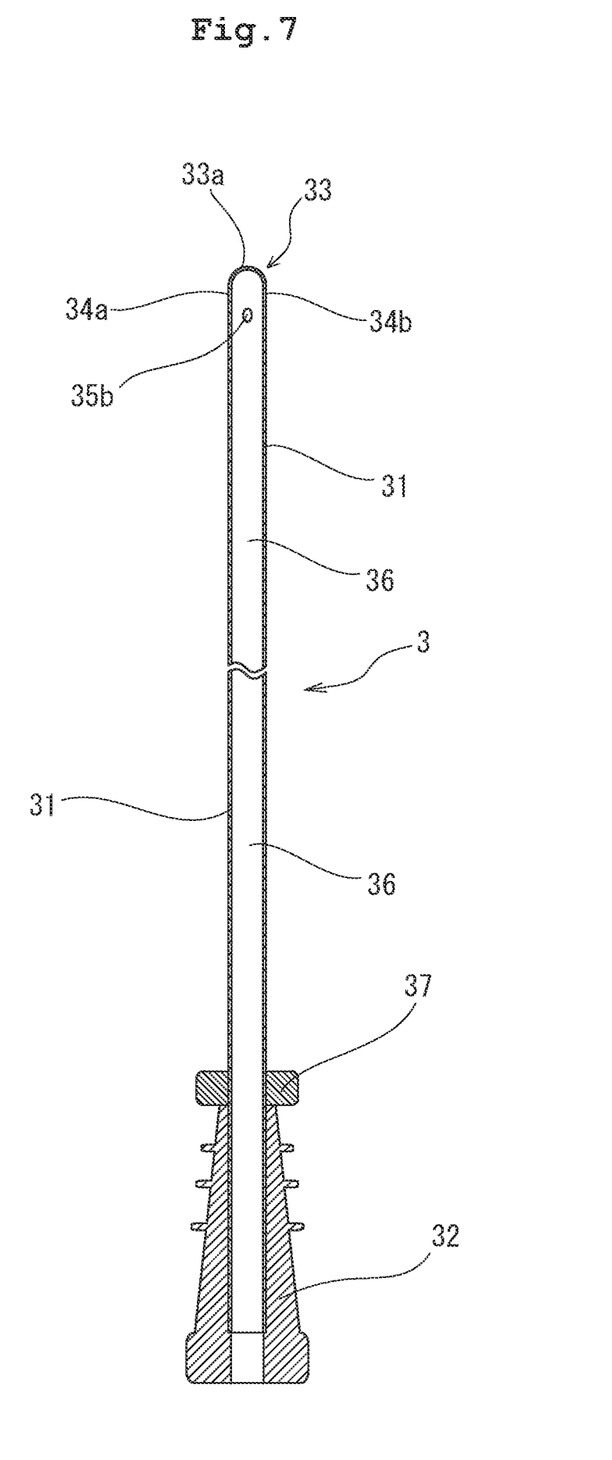
FIG. 7 is a longitudinal cross-sectional view of the flexible inner tube shown in FIG. 6.
Figure 8:
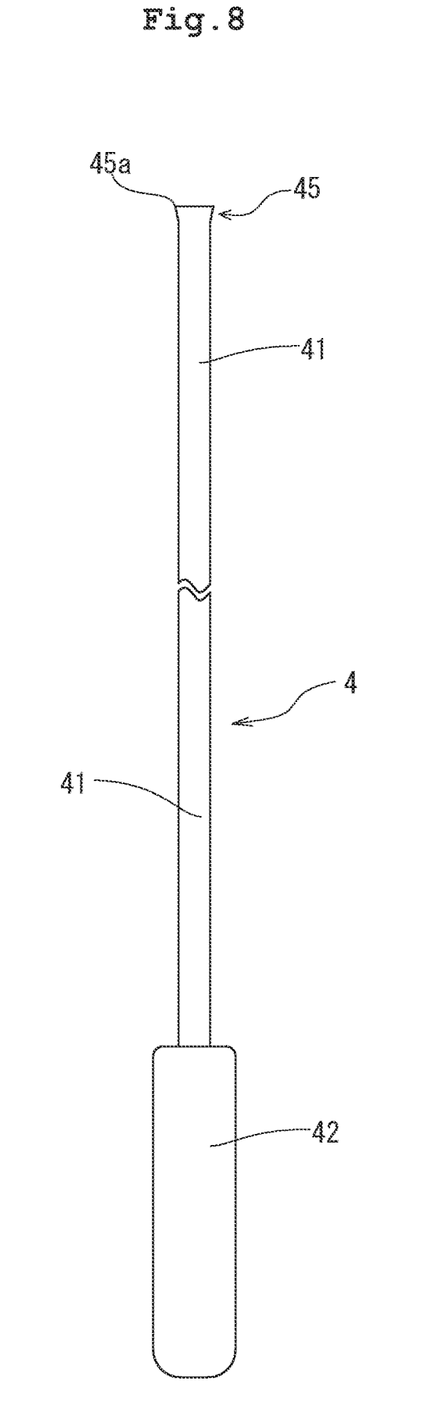
FIG. 8 is a partially omitted enlarged front view of a shaft member that is used in the intrauterine tissue collecting instrument shown in FIG. 1.

The outer tube distal end portion 23 can be inserted into the uterus. The outer tube distal end portion 23 includes the substantially semispherical distal end 23*a* and at least three slits 24 that extend from substantially the center of the distal end 23*a* toward the proximal end and in the direction of the side surface and are arranged at substantially equal angles with respect to the center axis of the flexible outer tube 2, and the outer tube distal end portion 23 can be open. In this embodiment, the outer tube distal end portion 23 includes four slits 24 that are arranged at substantially equal angles with respect to the center axis of the flexible outer tube 2 as shown in FIG. 4. The number of slits is preferably 3 to 8. The number of slits is particularly preferably 4 to 6.

The length of each slit 24 is preferably such that the slit starts from the top of the distal end 23a and ends at a distal end of a cylindrical portion of the outer tube main body 21. When pressed from the inside, the outer tube distal end portion 23 opens spreading outward (in the direction of the distal end) owing to the flexibility of the outer tube and the slits 24 described above. Thus, the inner tube distal end portion 33, which will be described later, is allowed to protrude from the distal end of the flexible outer tube 2. Note that in an unopened state, i.e., in a state where the inner tube distal end portion has never protruded, the outer tube distal end portion 23 is substantially a closed end. Furthermore, in this embodiment, the outer tube distal end portion 23 allows the flexible inner tube 3 to rotate within the flexible outer tube 2 in the state where the inner tube distal end portion 33 protrudes from the outer tube distal end portion 23.

The length of the outer tube main body 21 is 80 to 300 mm, and preferably 100 to 200 mm. The outer diameter of the outer tube main body is 1 to 6 mm, and preferably 1.5 to 5.0 mm. The inner diameter of the outer tube main body is 0.8 to 5.8 mm, and preferably 1.3 to 4.5 mm.

Figure 1:
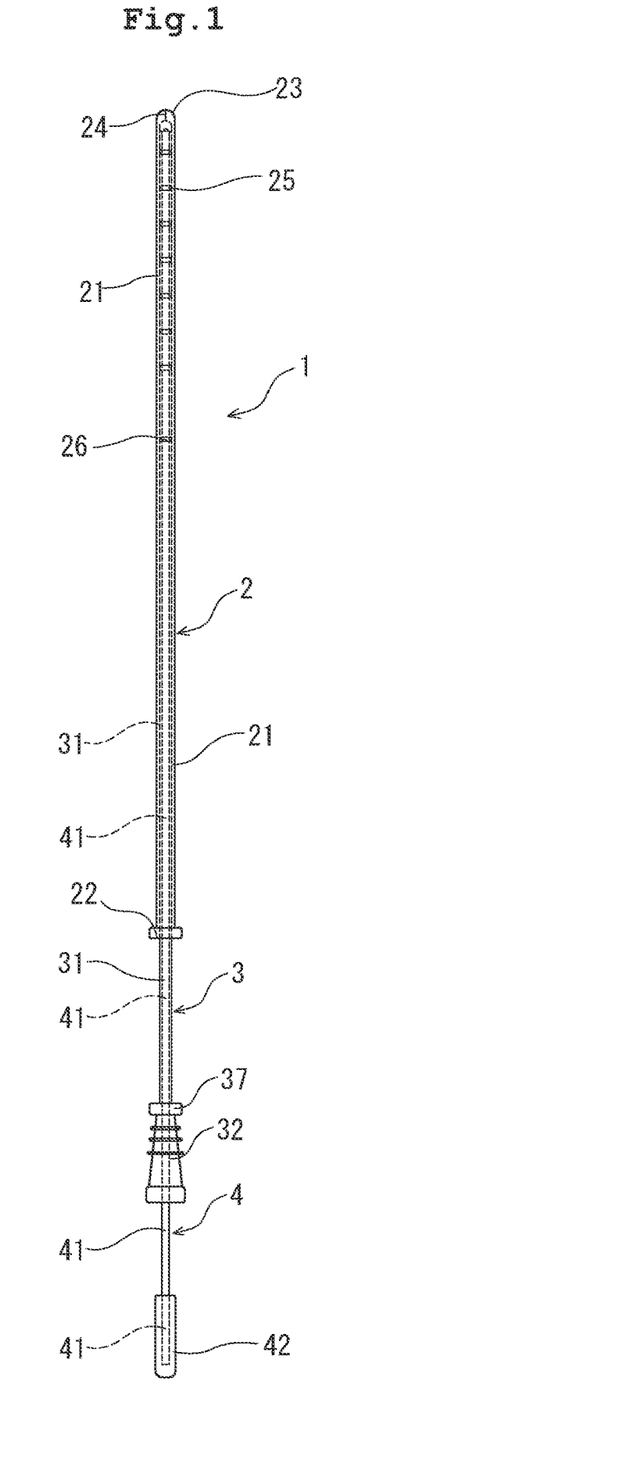
FIG. 1 is a front view of an embodiment of an intrauterine tissue collecting instrument according to the present invention.

The outer tube main body 21 is preferably formed from a material that has a certain degree of shape retainability. Examples of materials that can be used to form a flexible tube include polyesters, polyolefins (e.g., polyethylene, polypropylene, ethylene-propylene copolymer), polyamides (e.g., Nylon 6, Nylon 66), polyesters (e.g., polyethylene terephthalate), and fluororesins (e.g., PTFE, ETFE). Furthermore, it is preferable to provide a plurality of insertion depth check markers 26 on the external surface of the outer tube main body 21 as shown in FIG. 1.

In this embodiment, the outer tube hub 22 has a short cylindrical shape and is fixedly attached to a proximal end portion of the outer tube main body 21. Any of the materials described as examples of the material of the outer tube main body 21 can be suitably used to form the hub.

As shown in FIGS. 1, 2, 6, and 7, the flexible inner tube 3 includes an inner tube main body 31, the inner tube distal end portion 33 that is formed at the distal end of the inner tube main body 31, an inner tube hub 32 that is provided in a rear end portion of the inner tube main body 31, and a lumen 36. The flexible inner tube 3 can be extracted from the flexible outer tube 2.

The flexible inner tube 3 is inserted into the flexible outer tube 2 and is movable within the flexible outer tube 2 in the axial direction. Also, the flexible inner tube 3 is rotatable within the flexible outer tube 2. In this embodiment, an abutting portion (ring member) 37 is fixed to a proximal end portion of the inner tube main body 31 (forward of the distal end of the inner tube hub 32). In this embodiment, the abutting portion (ring member) 37 can abut against the proximal end portion of the flexible outer tube 2 (proximal end of the hub 22) and restricts movement of the flexible inner tube 3 in the direction of the distal end after the abutment. Accordingly, in the intrauterine tissue collecting instrument 1 of this embodiment, the flexible inner tube 2 has a restricted protrusible length of the inner tube distal end portion 33 from the outer tube distal end portion 23. Note that the protruding length may be restricted through abutment of the inner tube hub 32 against the proximal end portion of the flexible outer tube 2 (proximal end of the hub 22).

The inner tube distal end portion 33 includes a semispherical closed distal end 33a and the plurality of side openings 34a, 34b, 35a, and 35b provided on the proximal end side with respect to the closed distal end. The side openings 34a and 34b are provided facing each other, and similarly, the side openings 35a and 35b are provided facing each other. Note that the side openings 34a and 34b are shifted from the side openings 35a and 35b by approximately 90° with respect to the center axis of the flexible inner tube 3. Also, in a side surface of the inner tube main body 31, the side openings 34a and 34b are formed in a portion that is near the closed distal end 33a and is on the proximal end side with respect to the closed distal end, and the side openings 35a and 35b are located slightly closer to the proximal end than the side openings 34a and 34b are. The side openings 34a, 34b, 35a, and 35b may each have a perfect circle shape, an elliptical shape, an oval shape, or the like, and particularly preferably have an elliptical or oval shape that is elongated in the axial direction of the flexible inner tube 3.

The length of the inner tube main body 31 is 70 to 350 mm, and preferably 120 to 280 mm. The outer diameter of the inner tube main body is 0.5 to 4.5 mm, and preferably 0.7 to 4.3 mm. The inner diameter of the inner tube main body is 0.5 to 4.3 mm, and preferably 0.6 to 4.0 mm.

The inner tube main body 31 is preferably formed from a material that has a certain degree of shape retainability. Examples of materials that can be used to form the inner tube main body 31 include polyesters, polyolefins (e.g., polyethylene, polypropylene, ethylene-propylene copolymer), polyamides (e.g., Nylon 6, Nylon 66), polyesters (e.g., polyethylene terephthalate), and fluororesins (e.g., PTFE, ETFE).

A hard resin such as polystyrene, polyolefin (e.g., polyethylene, polypropylene), polycarbonate, polyamide, or the like can be suitably used to form the inner tube hub 32.

The ring member 37 preferably has a certain degree of elasticity in view of abutment against the proximal end portion of the flexible outer tube 2 (proximal end of the hub 22). Examples of materials that can be used to form the ring member include synthetic rubber such as urethane rubber, silicone rubber, and butadiene rubber, natural rubber such as latex rubber, soft vinyl chloride, polyolefins (polyethylene, polypropylene, ethylene-propylene copolymer, ethylene-vinyl acetate copolymer, a mixture of polypropylene and polyethylene or polybutene), polyesters (polyethylene terephthalate, polybutylene terephthalate), polyamides, elastomers such as polyolefin-based elastomer, polyamide-based elastomer, and styrene-based elastomer (e.g., styrene-butadiene-styrene copolymer, styrene-isoprene-styrene copolymer, styrene-ethylene-butylene-styrene copolymer), and polyurethanes, in particular, thermoplastic polyurethanes (thermoplastic polyether polyurethane, thermoplastic polyester polyurethane, particularly preferably segmented thermoplastic polyether polyurethane with soft and hard segment moieties, more specifically, the main component of the soft segment is preferably polytetramethylene ether glycol, polyethylene glycol, polypropylene glycol, or the like, and the main component of the hard segment is preferably 1,4-butanediol or the like).

The shaft member 4 is inserted into the flexible inner tube 3 and is movable within the flexible inner tube 3 in the axial direction as shown in FIGS. 1, 2, and 8 to 10. The shaft member 4 includes the diameter-expanded distal end portion 45 that slides within the flexible inner tube 3 in a liquid-tight manner and the core (metal inner core) 43 that is plastically deformable. The diameter-expanded distal end portion 45 is a flare-shaped diameter-expanded portion of which the diameter increases toward the distal end, and a resistance to movement of the shaft member 4 within the flexible inner tube 3 toward the distal end is higher than a resistance to movement of the shaft member 4 within the flexible inner tube 3 toward the proximal end. In other words, pushing the shaft member 4 within the flexible inner tube toward the distal end is harder than pulling the shaft member 4 within the flexible inner tube toward the proximal end.

Accordingly, it is easy to perform an operation for collecting intrauterine tissue into the inner tube distal end portion 33 of the flexible inner tube 3 (i.e., move the shaft member 4 toward the proximal end), and intrauterine tissue that is collected into the inner tube distal end portion 33 of the flexible inner tube 3 is unlikely to flow out by mistake.

Figure 9:
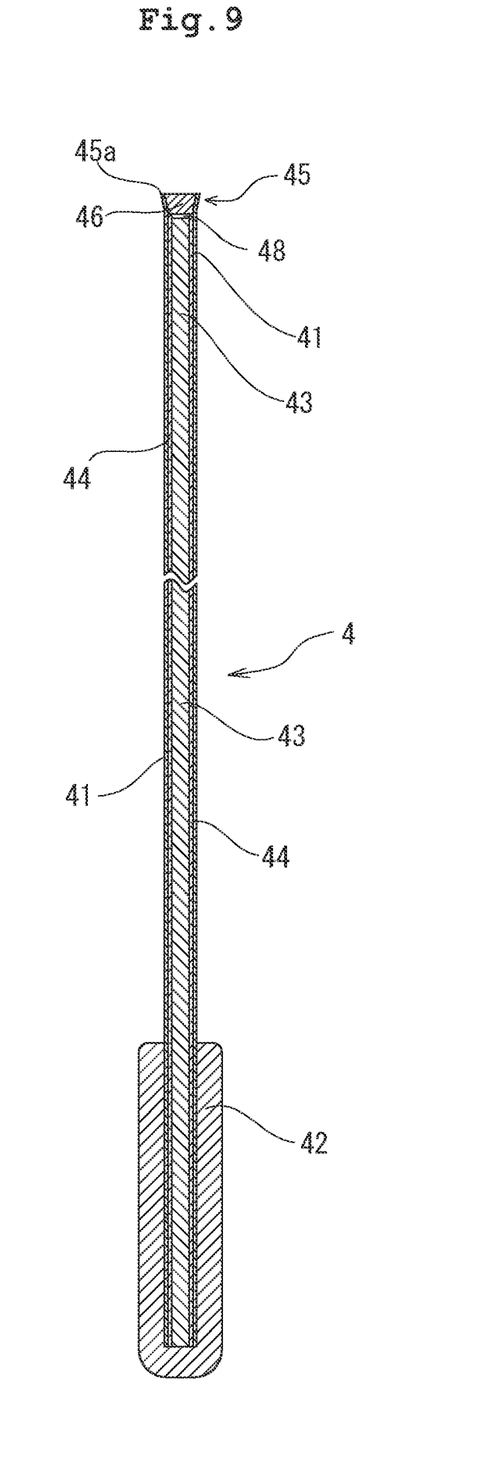
FIG. 9 is a longitudinal cross-sectional view of the shaft member shown in FIG. 8.
Figure 10:
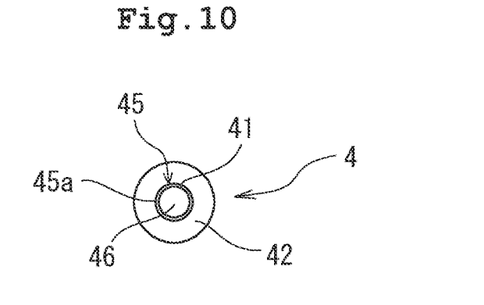
FIG. 10 is a plan view of the shaft member shown in FIG. 8.

As shown in FIG. 9, the shaft member 4 includes a shaft tube 41, the metal inner core 43 that is housed and fixed in the shaft tube 41, and an adhesive layer 44 that is located between the shaft tube 41 and the inner core 43. The diameter-expanded distal end portion (flare-shaped diameter-expanded portion) 45 is provided at the distal end of the shaft tube 41, and when the shaft member 4 moves within the flexible inner tube 3, a diameter-expanded end 45a of the diameter-expanded distal end portion 45 slides in a liquid-tight manner while being in close contact with the inner surface of the flexible inner tube 3. Also, there is a certain gap between the inner surface of the flexible inner tube 3 and an external surface of a portion of the shaft member 4 other than the diameter-expanded distal end portion (flare-shaped diameter-expanded portion) 45, and influence on a sliding resistance is avoided.

In this embodiment, the inside of the flare-shaped diameter-expanded portion 45 is filled with resin 46 as shown in FIG. 9 to restrict deformation of the diameter-expanded end 45a of the diameter-expanded distal end portion 45. Furthermore, in this embodiment, the distal end of the metal inner core 43 is spaced apart from the rear end of the resin filling the inside of the flare-shaped diameter-expanded portion 45 as shown in FIG. 9. Accordingly, there is a gap 48 between the resin 46 and the distal end of the metal inner core 43, and when the shaft member 4 is pressed toward the distal end, the metal inner core 43 does not directly press the flare-shaped diameter-expanded portion 45 (specifically, the filling resin 46).

The diameter-expanded end 45a of the diameter-expanded distal end portion 45 of the shaft member 4 has an outer diameter that is substantially the same as the inner diameter of the flexible inner tube 3. A difference between the outer diameter of the diameter-expanded end 45a and the minimum outer diameter of the diameter-expanded distal end portion 45 is preferably about 0.2 to 1 mm, and particularly preferably about 0.4 to 0.8 mm. The length of the shaft member 4 is 100 to 400 mm, and preferably 120 to 350 mm. The outer diameter of the portion of the shaft member 4 other than the diameter-expanded distal end portion 45 is smaller than the inner diameter of the flexible inner tube 3 preferably by 0.2 to 1.5 mm, and particularly preferably by 0.4 to 1.0 mm.

The core (inner core) 43 preferably has a certain degree of stiffness. Specifically, a plastically deformable metal rod-shaped member is suitably used as the inner core 43. The rod-shaped member may be solid or hollow. When a plastically deformable metal rod-shaped member is used as the inner core 43, the intrauterine tissue collecting instrument 1 can be curved and shaped by applying an external force to a portion of the intrauterine tissue collecting instrument 1 in which the shaft member 4 is located. A metal wire made of a stainless steel or the like is suitably used as the metal rod-shaped member, and a metal wire made of an annealed stainless steel is particularly preferable. The inner core 43 may be made of a semi-hard synthetic resin.

Examples of materials that can be used to form the shaft tube 41 include polyesters, polyolefins (e.g., polyethylene, polypropylene, ethylene-propylene copolymer), polyamides (e.g., Nylon 6, Nylon 66), polyesters (e.g., polyethylene terephthalate), and fluororesins (e.g., PTFE, ETFE).

The shaft tube 41 may also be formed using a flexible material. Examples of materials that can be used include synthetic rubber such as urethane rubber, silicone rubber, and butadiene rubber, natural rubber such as latex rubber, soft vinyl chloride, polyolefins (polyethylene, polypropylene, ethylene-propylene copolymer, ethylene-vinyl acetate copolymer, a mixture of polypropylene and polyethylene or polybutene), polyesters (polyethylene terephthalate, polybutylene terephthalate), polyamides, elastomers such as polyolefin-based elastomer, polyamide-based elastomer, and styrene-based elastomer (e.g., styrene-butadiene-styrene copolymer, styrene-isoprene-styrene copolymer, styrene-ethylene-butylene-styrene copolymer), and polyurethanes, in particular, thermoplastic polyurethanes (thermoplastic polyether polyurethane, thermoplastic polyester polyurethane, particularly preferably segmented thermoplastic polyether polyurethane with soft and hard segment moieties, more specifically, the main component of the soft segment is preferably polytetramethylene ether glycol, polyethylene glycol, polypropylene glycol, or the like, and the main component of the hard segment is preferably 1,4-butanediol or the like). Rubber such as silicone rubber or an elastomer is preferably used. Silicone rubber is particularly preferably used. Silicone rubber that has a 200% modulus of about 30 to 90 $kg/cm^2$, and preferably 40 to 60 $kg/cm^2$ is used as the silicone rubber.

The adhesive layer is not specifically limited, and can be formed using an acrylic-based adhesive, an epoxy-based adhesive, or a silicone-based adhesive, for example. Also, a tube-shaped grip portion 42 is provided in a rear end portion of the shaft member 4. The grip portion 42 is gripped when sliding the shaft.

Next, functions of the intrauterine tissue collecting instrument 1 according to the present invention will be described with reference to FIGS. 2 and 11 to 15.

The intrauterine tissue collecting instrument 1 according to the present invention can collect intrauterine tissue 5 through suction via the side openings 34a, 34b, 35a, and 35b of the flexible inner tube 3 when the shaft member 4 is moved toward the proximal end in a state where the inner tube distal end portion 33 protrudes from the outer tube distal end portion 23 within the uterus, and the inner tube distal end portion 33 protruding from the outer tube distal end portion 23 can be housed again in the flexible outer tube 2 within the uterus by moving the flexible inner tube 3 toward the proximal end.

Figure 2:
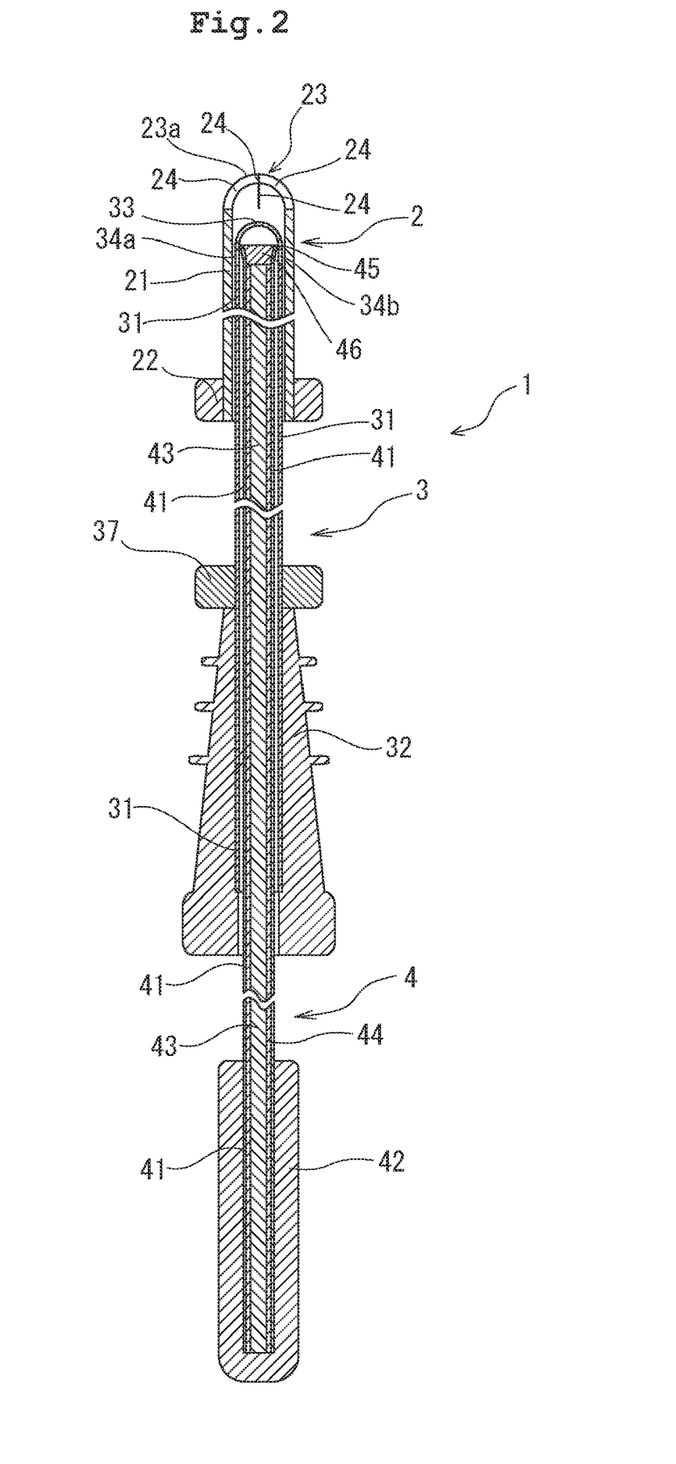
FIG. 2 is a partially omitted enlarged longitudinal cross-sectional view of the intrauterine tissue collecting instrument shown in FIG. 1.
Figure 3:
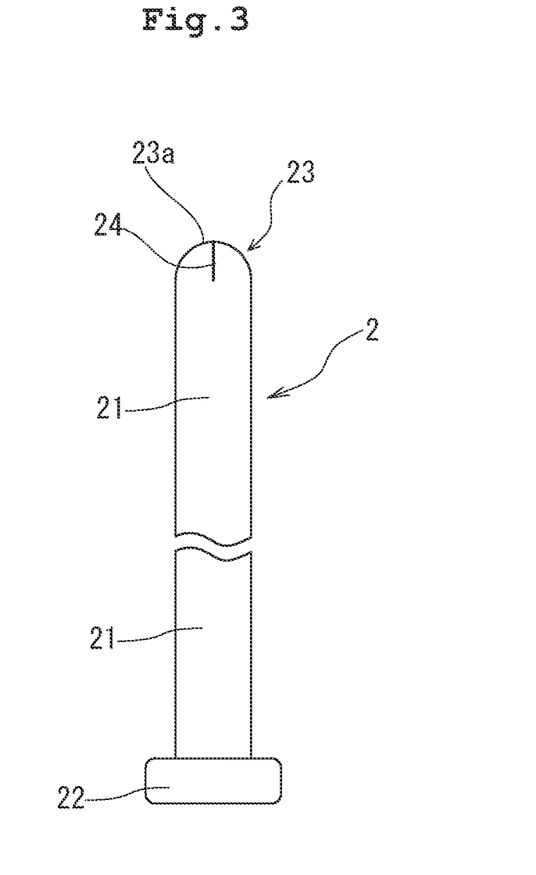
FIG. 3 is a partially omitted enlarged front view of a flexible outer tube that is used in the intrauterine tissue collecting instrument shown in FIG. 1.

A process of collecting the endometrium or the uterine fluid using the intrauterine tissue collecting instrument 1 according to the present invention will be described. After a vaginal speculum is inserted and the vagina is disinfected, the intrauterine tissue collecting instrument 1 is inserted through the cervical canal in a state where the inner tube distal end portion 33 of the flexible inner tube 3 is located within the outer tube distal end portion 23 of the flexible outer tube 2 and the diameter-expanded end 45a of the diameter-expanded distal end portion 45 of the shaft member 4 is located on the distal end side with respect to the side openings 34a and 34b of the inner tube 3 as shown in FIG.

2. Then, when the outer tube distal end portion of the flexible outer tube 2 has passed through the internal os of uterus, insertion of the flexible outer tube 2 of the intrauterine tissue collecting instrument 1 is ceased.

Figure 11:
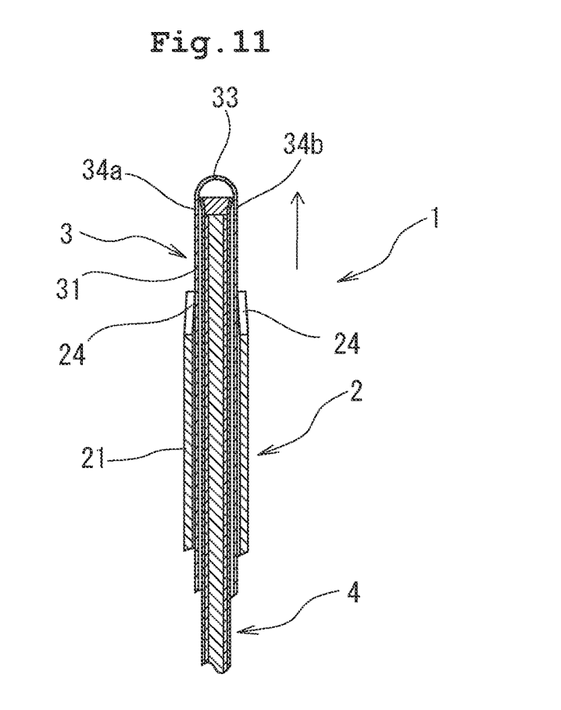
FIG. 11 is an illustrative diagram showing functions of the intrauterine tissue collecting instrument according to the present invention.
Figure 12:
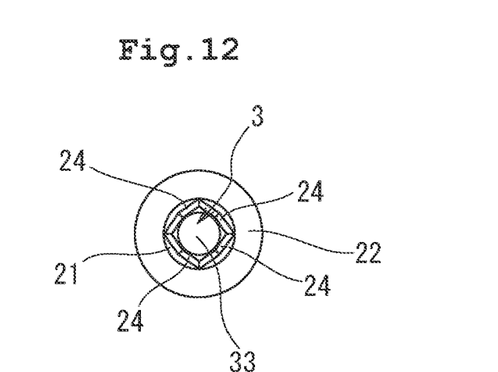
FIG. 12 is an illustrative diagram showing functions of the intrauterine tissue collecting instrument according to the present invention.

Subsequently, the flexible inner tube 3 is pushed together with the shaft member 4 while the position of the flexible outer tube 2 is maintained. The outer tube distal end portion 23 is pressed by the distal end portion of the flexible inner tube 3 progressed from the inside, and owing to the flexibility of the outer tube and the plurality of slits 24, the outer tube distal end portion 23 opens spreading outward (in the direction of the distal end), and the inner tube distal end portion 33 of the flexible inner tube 3 protrudes from the distal end of the flexible outer tube 2 and is exposed within the uterus as shown in FIG. 11. Note that the inner tube distal end portion 33 is pushed such that at least the entirety of a portion in which the side openings 34*a*, 34*b*, 35*a*, and 35*b* are formed is exposed within the uterus. In this state, as shown in FIGS. 11 and 12, a portion of the outer tube distal end portion 23 provided with the slits 24 spreads and the inner surface of the outer tube distal end portion 23 is in contact with the external surface of a portion of the inner tube distal end portion 33 where the side openings are not provided.

Figure 13:
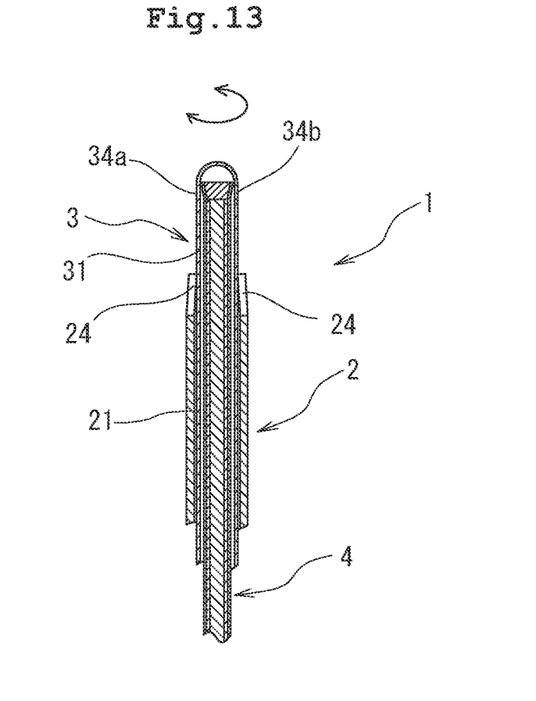
FIG. 13 is an illustrative diagram showing functions of the intrauterine tissue collecting instrument according to the present invention.

Note that the flexible inner tube 3 may be rotated together with the shaft member 4 within the flexible outer tube 2 as shown in FIG. 13 as necessary while the position of the flexible outer tube 2 is maintained.

Figure 14:
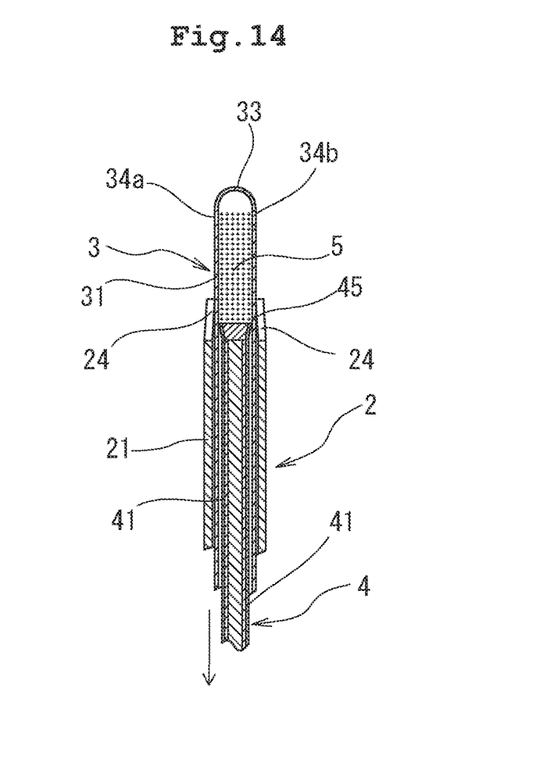
FIG. 14 is an illustrative diagram showing functions of the intrauterine tissue collecting instrument according to the present invention.

Subsequently, as shown in FIG. 14, only the shaft member 4 is pulled in the direction of the proximal end while positions of the flexible outer tube 2 and the flexible inner tube 3 are maintained. As a result, negative pressure is produced inside the flexible inner tube 3, and therefore, intrauterine tissue 5 near the side openings is collected into the inner tube distal end portion 33 of the flexible inner tube 3. Note that the flexible outer tube 2 may be rotated at the same time as the shaft member 4 is pulled in a state where the flexible outer tube 2 is held. In this case, positions of the side openings change and therefore intrauterine tissue can be collected well.

Figure 15:
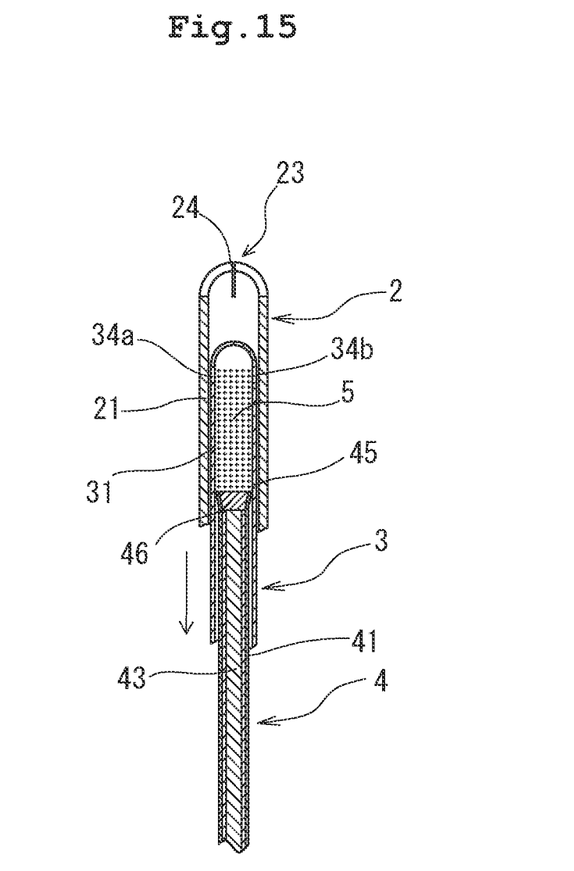
FIG. 15 is an illustrative diagram showing functions of the intrauterine tissue collecting instrument according to the present invention.

Then, after the intrauterine tissue has been collected, in the state where the position of the flexible outer tube 2 is maintained, the flexible inner tube 3 is moved (i.e., pulled) together with the shaft member 4 toward the proximal end within the uterus as shown in FIG. 15 to house the inner tube distal end portion 33 protruding from the outer tube distal end portion 23 again in the flexible outer tube 2 within the uterus. Subsequently, the entirety of the intrauterine tissue collecting instrument 1 is extracted from the body. In the above-described process, the inner tube distal end portion 33 of the flexible inner tube 3 and the collected intrauterine tissue 5 are not exposed except for inside the uterus, and therefore, a good specimen is collected. As necessary, the flexible inner tube 3 is extracted from the flexible outer tube 2 and the inner tube distal end portion 33 of the flexible inner tube 3 is cut off to collect the intrauterine tissue.

INDUSTRIAL APPLICABILITY

The intrauterine tissue collecting instrument according to the present invention is as follows.

(1) An intrauterine tissue collecting instrument comprising:

a flexible outer tube of which a distal end portion can be inserted into the uterus;

a flexible inner tube that is inserted into the flexible outer tube and is movable within the flexible outer tube in an axial direction; and a shaft member that is inserted into the flexible inner tube and is movable within the flexible inner tube in an axial direction, wherein the flexible outer tube includes an outer tube distal end portion that can be open and includes a substantially semispherical distal end and at least three slits that extend from substantially the center of the distal end toward a proximal end and in the direction of a side surface and are arranged at substantially equal angles with respect to a center axis of the flexible outer tube, the flexible inner tube includes an inner tube distal end portion that includes a closed distal end and a plurality of side openings that are provided on a proximal end side with respect to the closed distal end, the shaft member includes a diameter-expanded distal end portion that slides within the flexible inner tube in a liquid-tight manner and a core, the diameter-expanded distal end portion being a flare-shaped diameter-expanded portion of which the diameter increases toward a distal end, the shaft member has a higher resistance to movement toward the distal end side in the flexible inner tube than toward the proximal end side in the flexible inner tube, the flexible outer tube allows the inner tube distal end portion to protrude from the outer tube distal end portion by spreading slits formed portion when the flexible inner tube is pushed, and the intrauterine tissue collecting instrument can collect intrauterine tissue through suction via the side openings of the flexible inner tube when the shaft member is moved toward the proximal end in a state where the inner tube distal end portion protrudes from the outer tube distal end portion within the uterus, and the inner tube distal end portion protruding from the outer tube distal end portion can be housed again in the flexible outer tube within the uterus by moving the flexible inner tube toward the proximal end.

According to the intrauterine tissue collecting instrument, intrauterine tissue collecting instrument can collect intrauterine tissue through suction via the side openings of the flexible inner tube when the shaft member is moved toward the proximal end in a state where the inner tube distal end portion protrudes from the outer tube distal end portion within the uterus, and the inner tube distal end portion protruding from the outer tube distal end portion can be housed again in the flexible outer tube within the uterus by moving the flexible inner tube toward the proximal end, and therefore, contamination of the collected intrauterine tissue and the external surface of the collecting instrument can be prevented, and intrauterine tissue that serves as a good test specimen can be easily collected.

The intrauterine tissue collecting instrument described above may be embodied as described below.

(2) The intrauterine tissue collecting instrument according to above (1), wherein the intrauterine tissue collecting instrument can be curved and shaped by applying an external force to a portion of the intrauterine tissue collecting instrument in which the shaft member is located.

(3) The intrauterine tissue collecting instrument according to above (1) or (2), wherein the flexible inner tube is rotatable within the flexible outer tube in the state where the inner tube distal end portion protrudes from the outer tube distal end portion.

(4) The intrauterine tissue collecting instrument according to any one of above (1) to (3),
wherein the flexible inner tube includes an inner tube hub or an abutting portion that is provided in a proximal end portion of the flexible inner tube and can abut against a proximal end portion of the flexible outer tube, and the flexible inner tube has a restricted protrusible length of the inner tube distal end portion from the outer tube distal end portion.

(5) The intrauterine tissue collecting instrument according to any one of above (1) to (4),
wherein the flexible outer tube includes an outer tube hub that is provided in a proximal end portion of the flexible outer tube.

(6) The intrauterine tissue collecting instrument according to any one of above (1) to (5),
wherein the shaft member includes a shaft tube and the core that is housed and fixed in the shaft tube, the inside of the flare-shaped diameter-expanded portion is filled with resin, and a distal end of the core is spaced apart from a rear end of the resin filling the flare-shaped diameter-expanded portion.

(7) The intrauterine tissue collecting instrument according to any one of above (1) to (6),
wherein the flexible inner tube can be extracted from the flexible outer tube.

(8) The intrauterine tissue collecting instrument according to any one of above (1) to (7),
wherein graduations are provided on a side surface of the flexible outer tube.

(9) The intrauterine tissue collecting instrument according to any one of above (1) to (8),
wherein the flexible outer tube includes four slits as the slits, the four slits being arranged at substantially equal angles with respect to the center axis of the flexible outer tube.

(10) An intrauterine tissue collecting instrument comprising:
a flexible tube and a shaft member that is inserted into the flexible tube and is movable within the flexible in an axial direction,
wherein the flexible tube includes a tube distal end portion that includes a closed distal end and a plurality of side openings that are provided on a proximal end side with respect to the closed distal end,
the shaft member includes a diameter-expanded distal end portion that slides within the flexible tube in a liquid-tight manner and a core, the diameter-expanded distal end portion being a flare-shaped diameter-expanded portion of which the diameter increases toward a distal end, the shaft member has a higher resistance to movement toward the distal end side in the flexible tube than toward the proximal end side in the flexible tube, and
the intrauterine tissue collecting instrument can collect intrauterine tissue through suction via the side openings of the flexible tube when the shaft member is moved toward the proximal end within the uterus.

(11) The intrauterine tissue collecting instrument according to above (10),
wherein the shaft member includes a shaft tube and the core that is housed and fixed in the shaft tube, the inside of the flare-shaped diameter-expanded portion is filled with resin, and a distal end of the core is spaced apart from a rear end of the resin filling the flare-shaped diameter-expanded portion.

The invention claimed is:

1. An intrauterine tissue collecting instrument comprising:
a flexible outer tube having an outer tube distal end portion that is insertable into the uterus;
a flexible inner tube that is insertable into the flexible outer tube and is axially movable within the flexible outer tube; and
a shaft member that is insertable into the flexible inner tube and is axially movable within the flexible inner tube toward a distal end side of the flexible inner tube and toward a proximal end side of the flexible inner tube,
wherein the outer tube distal end portion includes a substantially semispherical distal end and at least three slits that extend from substantially a center of a surface of the substantially semispherical distal end toward a proximal end and in a direction of a side surface, and wherein the at least three slits are arranged at substantially equally angles with respect to a center axis of the flexible outer tube,
wherein the flexible inner tube includes an inner tube distal end portion that includes a closed distal end and a plurality of side openings that are provided on a proximal end side with respect to the closed distal end,
wherein the shaft member includes a diameter-expanded distal end portion that is slidable within the flexible inner tube in a liquid-tight manner, a shaft tube, and a metal inner core housed in and fixed to the shaft tube, the inner core having a most distal end, the diameter-expanded distal end portion being a flare-shaped diameter-expanded portion of which the diameter increases toward a distal end, and wherein the shaft member has a higher resistance to movement toward the distal end side in the flexible inner tube than toward the proximal end side in the flexible inner tube,
wherein the flexible outer tube is openable to allow the inner tube distal end portion to protrude from the outer tube distal end portion, wherein the flexible outer tube is configured to be opened by spreading parts of the outer tube distal end portion between the slits when the flexible inner tube is pushed,
wherein the flare-shaped diameter-expanded portion has an interior filled with resin, wherein the resin has a proximal rear end, and wherein the most distal end of the inner core is spaced apart from the proximal rear end of the resin that fills the flare-shaped diameter-expanded portion to define a gap between the proximal rear end of the resin and the most distal end of the inner core such that when the shaft member is pressed toward the distal end side, the inner core does not directly press the proximal rear end of the resin that fills the flare-shaped diameter-expanded portion, and
wherein the intrauterine tissue collecting instrument is configured to collect intrauterine tissue through suction via the side openings of the flexible inner tube when the shaft member is moved toward the proximal end side in the flexible inner tube in a state where the inner tube distal end portion protrudes from the outer tube distal end portion within the uterus, and wherein the inner tube distal end portion protruding from the outer tube distal end portion is movable to a position housed again in the flexible outer tube within the uterus by moving the flexible inner tube toward the proximal end.

2. The intrauterine tissue collecting instrument according to claim 1,
wherein the intrauterine tissue collecting instrument is configured to be curved and shaped by applying an external force to a portion of the intrauterine tissue collecting instrument in which the shaft member is located.

3. The intrauterine tissue collecting instrument according to claim 1,
wherein the flexible inner tube is rotatable within the flexible outer tube in the state where the inner tube distal end portion protrudes from the outer tube distal end portion within the uterus.

4. The intrauterine tissue collecting instrument according to claim 1,
wherein the flexible inner tube includes an inner tube hub or an abutting portion that is provided in a proximal end portion of the flexible inner tube and is configured to abut against a proximal end portion of the flexible outer tube, and wherein the inner tube hub or the abutting portion is configured to restrict a protrusible length of the inner tube distal end portion from the outer tube distal end portion.

5. The intrauterine tissue collecting instrument according to claim 1,
wherein the flexible outer tube includes an outer tube hub that is provided in a proximal end portion of the flexible outer tube.

6. The intrauterine tissue collecting instrument according to claim 1,
wherein the flexible inner tube is extractable from the flexible outer tube.

7. The intrauterine tissue collecting instrument according to claim 1,
wherein the flexible outer tube includes four slits as the slits, the four slits being arranged at substantially equal angles with respect to the center axis of the flexible outer tube.

8. The intrauterine tissue collecting instrument according to claim 1, wherein the inner core is fixed to the shaft tube by way of an adhesive layer.

9. The intrauterine tissue collecting instrument according to claim 1, wherein the diameter of the flare-shaped diameter-expanded portion increases toward the distal end such that a maximum outer diameter of the flare-shaped diameter-expanded portion is located at a most distal end of the shaft member.

10. An intrauterine tissue collecting instrument comprising:
a flexible tube and a shaft member, the shaft member being insertable into the flexible tube and being axially movable within the flexible tube toward a distal end side and toward a proximal end side,
wherein the flexible tube includes a tube distal end portion that includes a closed distal end and a plurality of side openings that are provided on a proximal end side with respect to the closed distal end,
wherein the shaft member includes a diameter-expanded distal end portion that is slidable within the flexible tube in a liquid-tight manner, a shaft tube, and a metal inner core housed in and fixed to the shaft tube, the inner core having a most distal end, the diameter-expanded distal end portion being a flare-shaped diameter-expanded portion of which the diameter increases toward a distal end of the diameter-expanded distal end portion, and wherein the shaft member has a higher resistance to movement toward the distal end side in the flexible tube than toward the proximal end side in the flexible inner tube,
wherein the flare-shaped diameter-expanded portion has an interior filled with resin, wherein the resin has a proximal rear end, and wherein the most distal end of the inner core is spaced apart from the proximal rear end of the resin that fills the flare-shaped diameter-expanded portion to define a gap between the proximal rear end of the resin and the most distal end of the inner core such that when the shaft member is pressed toward the distal end side, the inner core does not directly press the proximal rear end of the resin that fills the flare-shaped diameter-expanded portion, and
wherein the intrauterine tissue collecting instrument is configured to collect intrauterine tissue through suction via the side openings of the flexible tube when the shaft member is moved toward the proximal end side in the flexible tube within the uterus.

11. The intrauterine tissue collecting instrument according to claim 10, wherein the inner core is fixed to the shaft tube by way of an adhesive layer.

12. The intrauterine tissue collecting instrument according to claim 10, wherein the diameter of the flare-shaped diameter-expanded portion increases toward the distal end such that a maximum outer diameter of the flare-shaped diameter-expanded portion is located at a most distal end of the shaft member.

* * * * *